United States Patent
Wang

(10) Patent No.: US 10,383,692 B1
(45) Date of Patent: Aug. 20, 2019

(54) SURGICAL INSTRUMENT GUIDANCE SYSTEM

(71) Applicant: TAIWAN MAIN ORTHOPAEDIC BIOTECHNOLOGY CO., LTD., Taichung (TW)

(72) Inventor: Min-Liang Wang, Taichung (TW)

(73) Assignee: TAIWAN MAIN ORTHOPAEDIC BIOTECHNOLOGY CO., LTD., Taichung (TW)

( * ) Notice: Subject to any disclaimer, the term of this patent is extended or adjusted under 35 U.S.C. 154(b) by 0 days.

(21) Appl. No.: 15/953,088

(22) Filed: Apr. 13, 2018

(51) Int. Cl.
| | |
|---|---|
| *A61B 34/20* | (2016.01) |
| *A61B 90/00* | (2016.01) |
| *A61B 34/10* | (2016.01) |
| *A61B 34/00* | (2016.01) |
| *A61B 90/50* | (2016.01) |
| *G06T 19/00* | (2011.01) |

(52) U.S. Cl.
CPC ............ *A61B 34/20* (2016.02); *A61B 90/361* (2016.02); *G06T 19/006* (2013.01); *A61B 2034/107* (2016.02); *A61B 2034/2057* (2016.02); *A61B 2034/252* (2016.02); *A61B 2090/372* (2016.02); *A61B 2090/373* (2016.02); *A61B 2090/502* (2016.02)

(58) Field of Classification Search
CPC ..... G06T 19/006; A61B 34/20; A61B 90/361; A61B 2034/107; A61B 2034/2057; A61B 2034/252; A61B 2090/372; A61B 2090/373; A61B 2090/502
See application file for complete search history.

(56) References Cited

U.S. PATENT DOCUMENTS

| | | | | |
|---|---|---|---|---|
| 8,553,935 | B2* | 10/2013 | Mandella | G01B 21/04 382/103 |
| 2016/0324580 | A1* | 11/2016 | Esterberg | A61B 34/10 |
| 2018/0228555 | A1* | 8/2018 | Charron | A61B 90/37 |
| 2018/0310831 | A1* | 11/2018 | Cheng | A61B 34/20 |
| 2019/0011709 | A1* | 1/2019 | Yadav | A61B 90/37 |
| 2019/0053855 | A1* | 2/2019 | Siemionow | G02B 27/017 |

FOREIGN PATENT DOCUMENTS

| | | |
|---|---|---|
| TW | 201801682 A | 1/2018 |
| WO | 2018/010040 A1 | 1/2018 |

* cited by examiner

*Primary Examiner* — Ke Xiao
*Assistant Examiner* — Jed-Justin Imperial
(74) *Attorney, Agent, or Firm* — Pai Patent & Trademark Law Firm; Chao-Chang David Pai

(57) ABSTRACT

Using the surgical instrument guidance system of the present invention, a doctor can instantly obtain a real field of view of a surgical site of a patient, a three-dimensional medical image that coincides with a surgical site of the patient, and a real-time positional relationship between the surgical instrument and the surgical site of the patient. The surgical instrument guidance system provides an entrance guiding interface, an angle guiding interface and a depth guiding interface to help the surgeon monitor whether the position relationship between the surgical instrument and the patient's surgical site conforms to the preoperative planning and specifically increases the accuracy of position, angle and depth of the surgical instrument on the surgical site of the patient.

6 Claims, 5 Drawing Sheets

SURGICAL INSTRUMENT GUIDANCE SYSTEM

BACKGROUND OF THE INVENTION

1. Field of the Invention

The present invention relates to the field of medical technology. More particularly, the present invention relates to a surgical instrument guidance system used in surgery to solve the problem of the positional relationship between the surgical instrument and the surgical site of the patient.

2. Description of the Related Art

During the medical procedure, the physician must confirm the position of the surgical site and the location of the surgical knife with the help of images such as X-rays, computed tomography (CT) or magnetic resonance imaging (MRI), which are presented on the overhead display of the operating room. Physicians, such as surgeons, need to bow down to see the surgical site while operating the site but also frequently look up or turn around to watch the display screen, making it difficult to quickly and accurately determine the surgical site and the position under the surgical knife.

Since the lesion is not exposed and the lesion is not located at the site where the endoscopic surgery can be performed, it is difficult for the physician to determine whether the probe is punctured as the probe passes through human skin and muscles into the human body to do tissue sampling of the lesion. If the same lesion needs to be sampled at different positions or depths, the probe position will be harder to precisely set up.

For traditional orthopedic surgeons, the orthopedists usually locate surgical instruments or implants based on skeletal anatomy, pre-operative medical imaging data, and X-ray images of intraoperative patients. However, even for orthopedists having very rich orthopedic surgical experience, large deviations of positioning accuracy could still occur.

BRIEF SUMMARY OF THE INVENTION

An object of the present invention is to provide a surgical instrument guidance system for use in surgery, to solve the problem of the positional relationship between the aforementioned surgical instrument and the surgical site of the patient.

A surgical instrument guidance system of the present invention comprises:

a preoperative planning system, used to import a three-dimensional medical image of a surgical site of a patient and use the three-dimensional medical image to define an entrance point, an endpoint, and a reference angle of a surgical instrument passing through the entrance point and the endpoint;

a camera system, built in a pair of smart glasses, used to capture real-time dynamic images of the surgical site of the patient and a surgical instrument movement track;

an image coincidence system, used to import the three-dimensional medical image of the preoperative planning system and display the three-dimensional medical images on the display screen of the smart glasses, wherein the three-dimensional medical images and the real field of vision of the patient's surgical site viewed by the doctor are matched in coincidence;

a real-time surgical instrument tracking system, through the real-time dynamic image of a surgical instrument movement track captured by the camera system, used to (a) calculate in real-time a position difference between the tail point of the surgical instrument and the entrance point of the preoperative planning system, (b) to calculate in real-time an angle difference between the tail point to a top point of the surgical instrument and the reference angle of the preoperative planning system, and (c) to calculate in real-time a distance difference between the tail point of the surgical instrument and the end point of the preoperative planning system; wherein the position difference is displayed through an entrance guiding interface, such that when the tail point of the surgical instrument is aligned with the entrance point, the entrance guiding interface displays an entrance aiming information, and when the tail point of the surgical instrument deviates from the entrance point, the entrance guiding interface displays an entrance deviation information; wherein the angle difference is displayed through an angle guiding interface, such that when the angle of the surgical instrument is aligned with the reference angle, the angle guiding interface displays an angle alignment information, and when the angle of the surgical instrument deviates from the reference angle, the angle guiding interface displays an angle deviation information; wherein the distance difference is displayed through a depth guiding interface, such that when the tail point of the surgical instrument touches the end point, the depth guiding interface displays a touched information, and when there is a distance difference between the tail point of the surgical instrument and the end point, the depth guiding interface displays an untouched information. The entrance guiding interface, the angle guiding interface, and the depth guiding interface are presented in the display screen of the smart glasses or in a real scene viewed through the smart glasses. Alternatively, through Mixed Reality (MR) technology, the entrance guiding interface, the angle guiding interface, and the depth guiding interface are presented in real-time in a real scene viewed through the smart glasses.

The efficacy of the present invention:

Through the smart glasses, the doctor can instantly obtain the true field of view of the surgical site of the patient, the three-dimensional medical image that coincides with the surgical site of the patient, and the real-time positional relationship between the surgical instruments and the surgical site of the patient. With the entrance guiding interface, the angle guiding interface, and the depth guiding interface, the doctor can monitor specifically and instantly whether the position relationship between the surgical instrument and the patient's surgical site conforms to the preoperative planning, and specifically increases the accuracy of the surgical instrument on the surgical site of the patient.

DETAILED DESCRIPTION OF THE INVENTION

In order to make the objectives, technical solutions and advantages of the present invention more comprehensible, the present invention will be further described in detail below with reference to the accompanying drawings and embodiments. It should be understood that the specific embodiments described herein are merely used to explain the present invention, and are not intended to limit the present invention.

Figure 5:
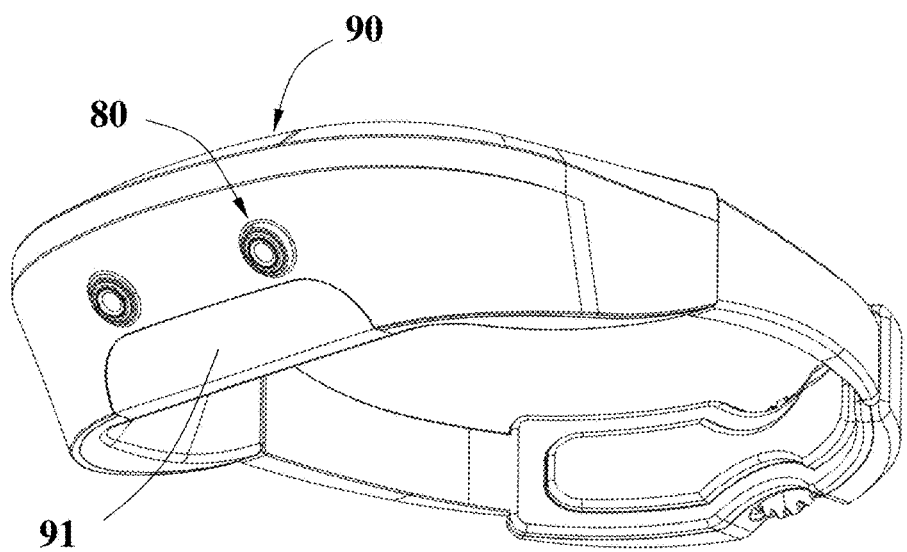
FIG. 5 is a schematic view of the camera system and the smart glasses according to the present invention.

Please refer to FIG. 5, it is a schematic view of the camera system and the smart glasses according to the present invention. The surgical instrument guidance system of the present invention comprises: a preoperative planning system, a camera system 80, a pair of smart glasses 90, an image coincidence system and a real-time surgical instrument tracking system.

Figure 1:
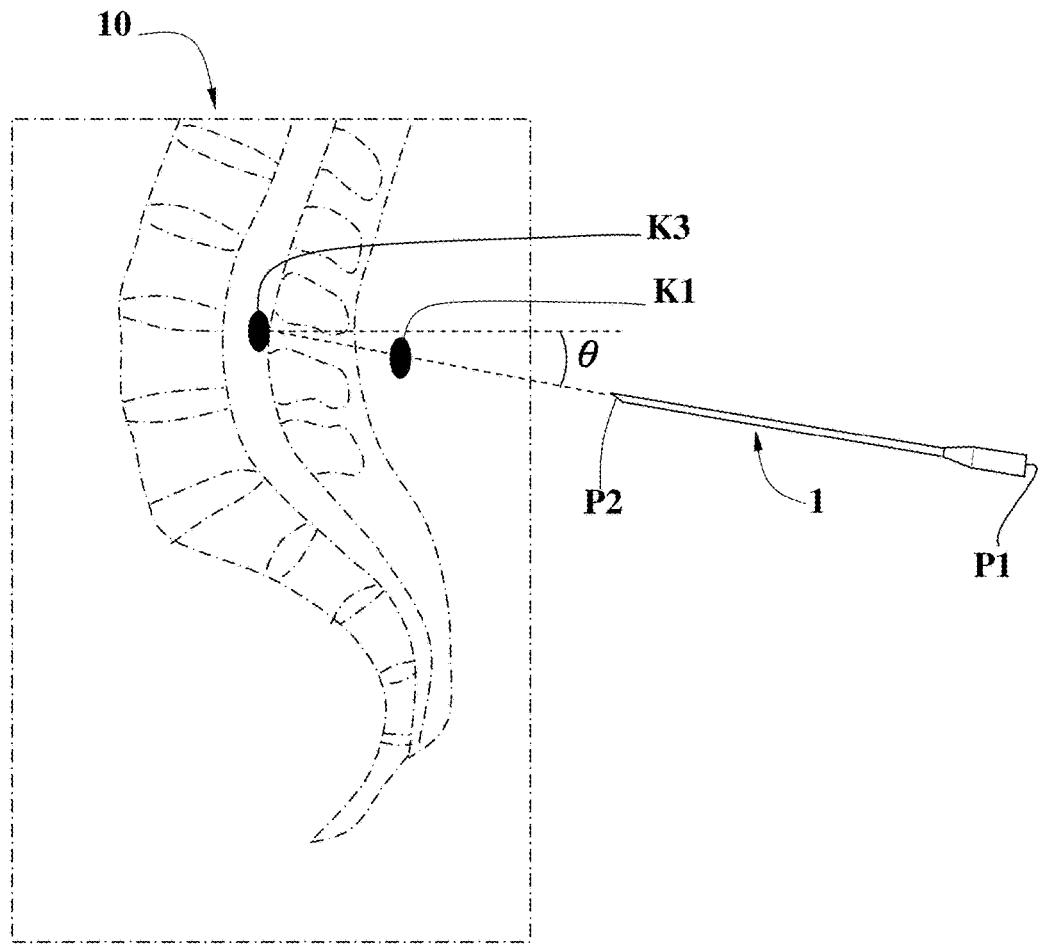
FIG. 1 is a schematic view of the present invention defining the entrance point, the end point and the reference angle of a surgical instrument in a two-dimensional medical image.

The preoperative planning system is used for the construction of preoperative plan information for the doctor/physician. The preoperative plan information includes the two-dimensional medical images and three-dimensional medical images of the surgical site of the patient. As shown in FIG. 1, the two-dimensional medical image 10 and/or the three-dimensional medical image define an entrance point K1, an end point K3 of the surgical instrument 1 and a reference angle θ of the surgical instrument passing through the entrance point K1 and the end point K3, θ.

As shown in FIG. 5, the camera system 80 is used for capturing the patient's surgical site and a real-time dynamic image of a surgical instrument movement track. The camera system 80 is built in smart glasses 90 worn by doctors/physicians. The camera system 80 uses one or more cameras of the same or different functions, including but not limited to IR camera, Color camera, Depth camera and CCD camera. For example, two cameras are used in an embodiment, one is a CCD camera, and the other is the IR Camera.

Figure 6:
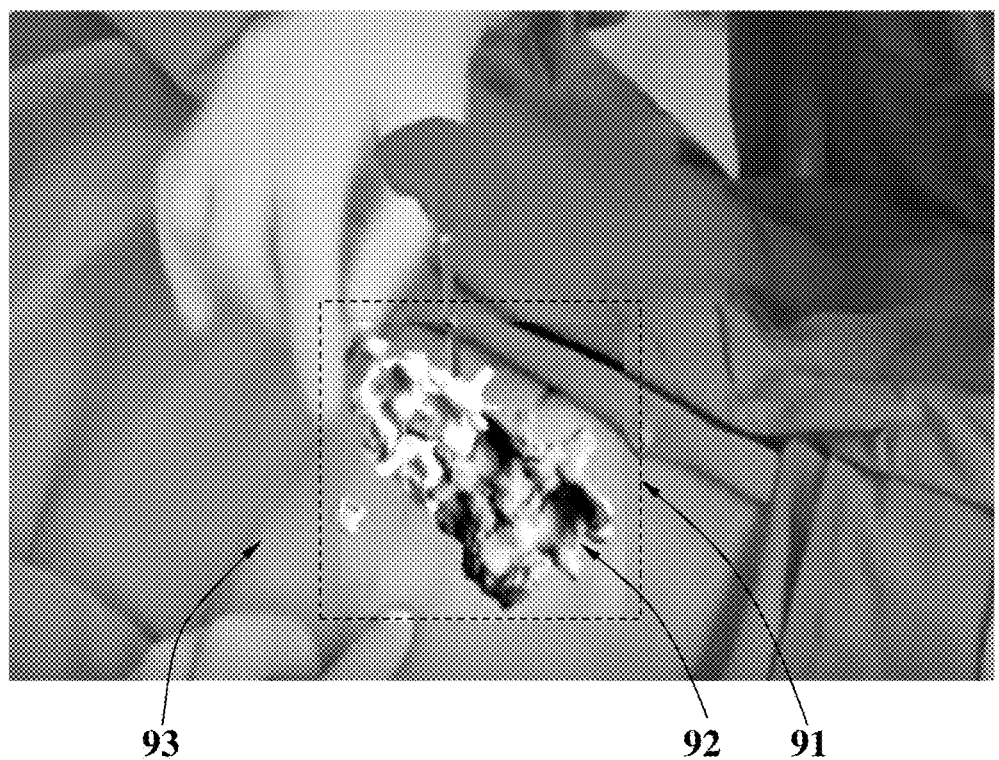
FIG. 6 is a schematic diagram of the present invention in which a smart glasses displays a three-dimensional medical image and coincides with the true field of view of the surgical site of the patient.

FIG. 6 is a schematic diagram of the present invention in which a smart glasses displays a three-dimensional medical image and coincides with the true field of view of the surgical site of the patient. As shown in FIG. 6, the image coincidence system is used to import a three-dimensional medical image of the preoperative planning system and displays the three-dimensional medical image 92 on the display screen 91 of the smart glasses 90. The image coincidence system adjusts an angle of the three-dimensional medical image 92 on the display screen 91 according to a focal length and a viewing angle of the doctor's eyes and causes the three-dimensional medical images 92 to be coincident with a real field of view of a doctor viewing the surgical site of the patient. In the embodiment of the present invention, a method for enhancing the image reality (PCT Patent Application No. PCT/CN2016/000374) is adopted to obtain the correct position of the doctor's eye on the marked point of the surgical site of the patient so as to adjust the error between the three-dimensional medical image and marked point.

Figure 2:
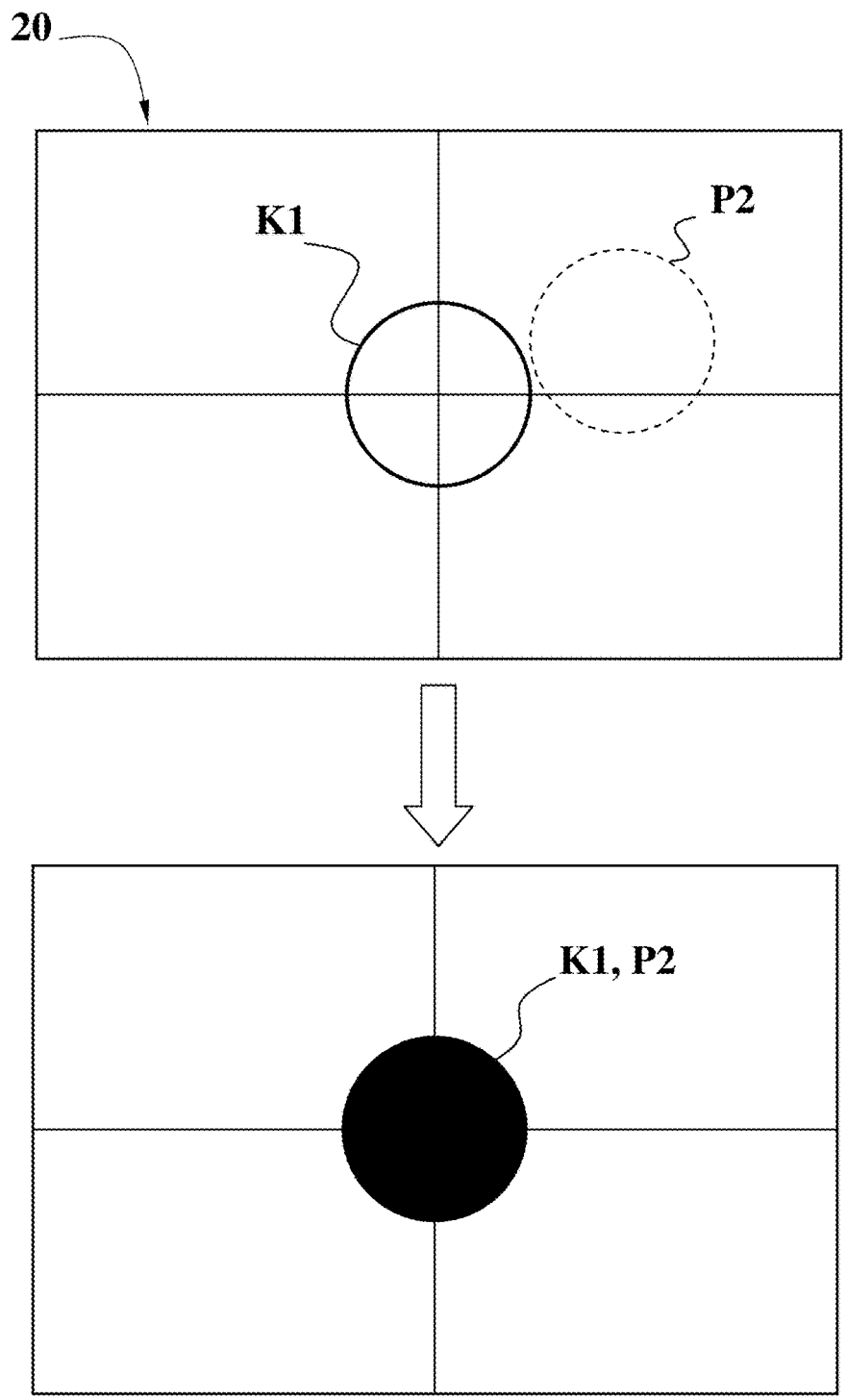
FIG. 2 is a schematic diagram of an entrance guiding interface according to the present invention.

The real-time surgical instrument tracking system, through the real-time dynamic image of a surgical instrument movement track captured by the camera system, is used to (1) calculates in real-time a position difference between the tail point P2 (as shown in FIG. 1) of the surgical instrument and the entrance point K1 of the preoperative planning system. The position difference is displayed through the entrance guiding interface 20 (as shown in FIG. 2). When P2 and K1 are aligned, the entrance guiding interface 20 displays an entrance aiming information (for example, the entrance guiding interface 20 presents a green color). When P2 deviates from K1, the entrance guiding interface 20 displays an entrance deviation information (for example, the entrance guiding interface 20 presents a red color). The change of the color is a way to show the entrance aiming information or the entrance deviation information, however, the change of the color is not limited to this. In the embodiment of the present invention, K1 is presented as a solid open hollow circle, P2 is presented as a dotted hollow circle, indicating that the circle of P2 is real-time displacement due to the movement of the surgical instrument (a displacement mark), and the circle of K1 is fixed (a fixed mark). The deviation information is that the circle of P2 and the circle of K1 (the displacement mark and the fixed mark) do not coincide, and the entrance aiming information is that the circle of P2 and the circle of K1 coincide and show a solid fill.

Figure 3:
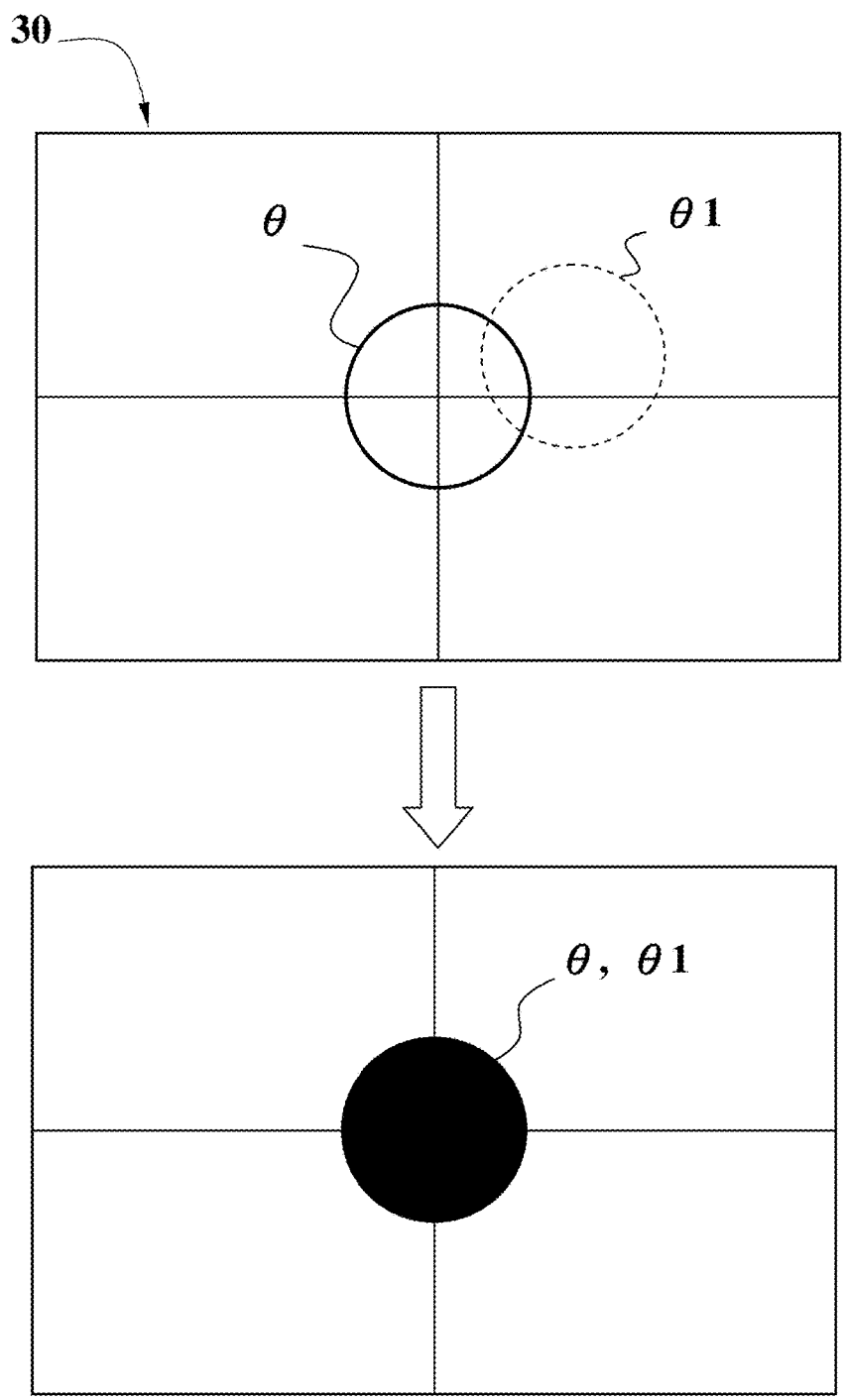
FIG. 3 is a schematic diagram of the angle guiding interface of the present invention.

The real-time surgical instrument tracking system also calculates in real-time the angle difference between the angle θ1 of the tail end P2 of the surgical instrument to the top point P1 (as shown in FIG. 1) and the reference angle θ of the preoperative planning system. The angle difference is displayed through the angle guiding interface 30 (as shown in FIG. 3). When θ1 and θ are aligned, the angle guiding interface 30 displays an angle alignment information (for example, the angle guiding interface 30 presents a green color). When θ1 deviates from θ, the angle guiding interface 30 displays an angle deviation information (for example, the angle guiding interface 30 presents a red color). The change of color is a way to show the angle alignment information or the angle deviation information, however, the change of the color is not limited to this. In the embodiment of the present invention, θ is presented as a solid open hollow circle, θ1 is presented as a dotted hollow circle, representing that the circle of θ1 is real-time displacement due to the movement of the surgical instrument (a displacement mark), and the circle of θ is fixed (a fixed mark). The angle deviation information is that the circle of θ1 and the circle of θ (the displacement mark and the fixed mark) do not coincide, and the angle alignment information is that the circle of θ1 and the circle of θ coincide and show a solid fill.

Figure 4:
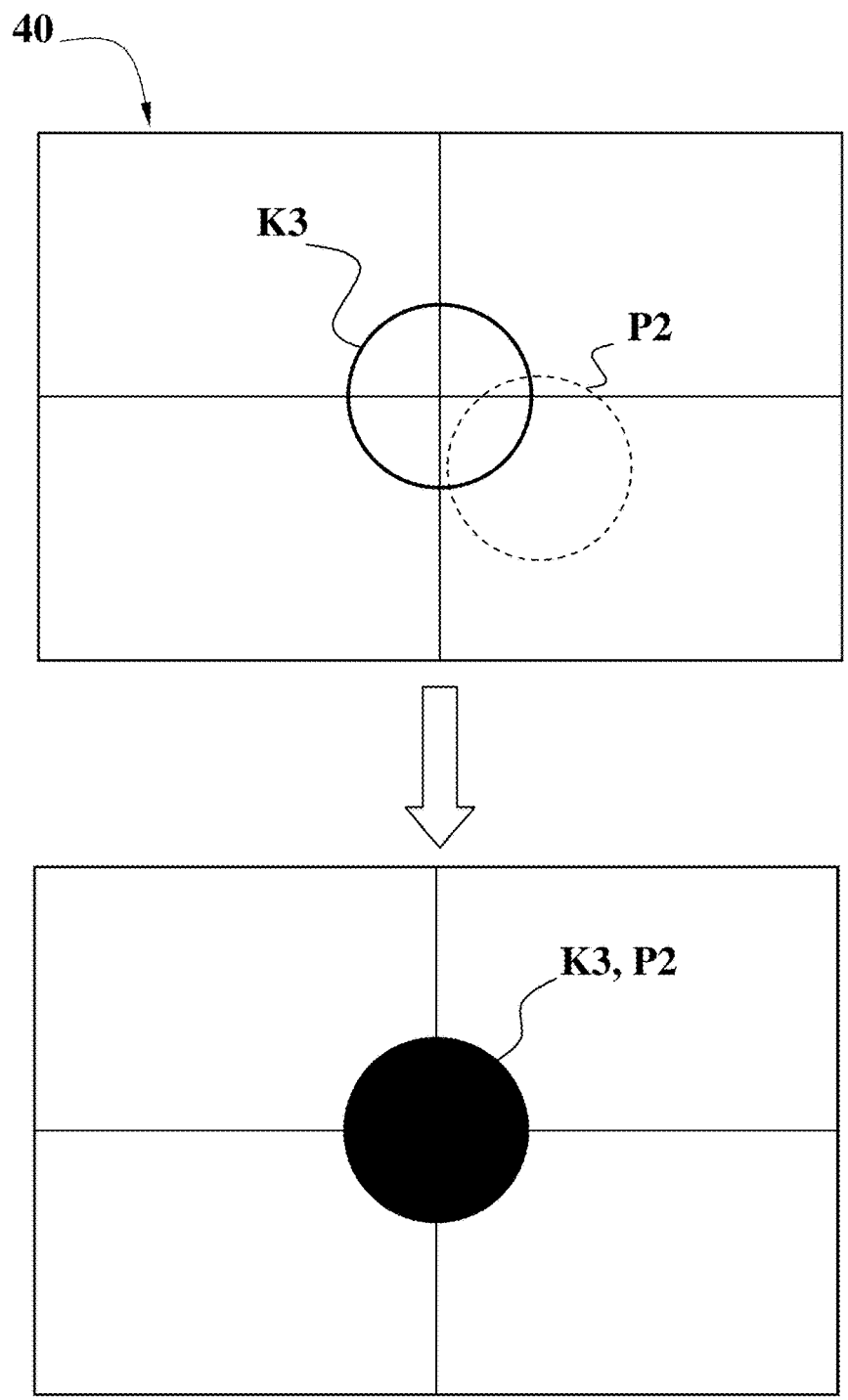
FIG. 4 is a schematic diagram of a depth guiding interface according to the present invention.

The real-time surgical instrument tracking system also calculates in real-time the distance difference between the tail end P2 of the surgical instrument and the end point K3 of the preoperative planning system. The distance difference is displayed through the depth guiding interface 40 (as shown in FIG. 4). When P2 and K3 are aligned, the depth guiding interface 40 displays an touched information (for example, the depth guiding interface 40 presents a green color). When P2 deviates from K3, the depth guiding interface 40 displays an untouched information (for example, the depth guiding interface 40 presents a red color). The change of color is a way to show the touched information or the untouched information, however, the change of the color is not limited to this. In the embodiment of the present invention, K3 is presented as a solid open hollow circle, P2 is presented as a dotted hollow circle, representing that the circle of P2 is real-time displacement due to the movement of the surgical instrument (a displacement mark), and the circle of K3 is fixed (a fixed mark). The untouched information is that the circle of P2 and the circle of K3 (the displacement mark and the fixed mark) do not coincide, and the touched information is that the circle of P2 and the circle of K3 coincide and show a solid fill.

The entrance guiding interface 20, the angle guiding interface 30, and the depth guiding interface 40 are displayed on the display screen 91 of the smart glasses 90, and such the interfaces do not coincide with the three-dimensional medical images 93 displayed on the display screen 91 of the smart glasses 90 firstly. The real-time surgical instrument tracking system continuously monitors the position, angle, and depth of the surgical instrument 1 during the operative procedure. Entrance, angle and depth guidelines are to be met in order. First, when the entrance aiming information appears and continues to be maintained, the angle guiding interface 30 is started. When both the entrance aiming information and the angle alignment information appear and are continuously maintained. The depth guiding interface 40 is started. When the touched information appears, indicating that the surgical instrument 1 enters the patient's surgical site in accordance with the entrance point K1 and the reference angle θ of the preoperative planning system and touches the end point K3.

Through the smart glasses 90, a doctor can instantly obtain a real scene of the surgical site of the patient, a three-dimensional medical image that coincides with a surgical site of the patient, and a real-time positional relationship between the surgical instrument and the surgical site of the patient. In the entrance guiding interface 20, the angle guiding interface 30, and the depth guiding interface 40, the doctor can monitor specifically and instantly whether the positional relationship between the surgical instrument and the patient's surgical site conforms to the preoperative planning, and specifically increases the accuracy of the surgical instrument on the surgical site of the patient.

In addition, through the mixed reality (Mixed Reality) technology, the entrance guiding interface, the angle guiding interface, and the depth guiding interface are presented in real-time in a real scene viewed through the smart glasses.

What is claimed is:

1. A surgical instrument guidance system, comprising:
    a preoperative planning system, which imports a two-dimensional medical image and a three-dimensional medical image of a surgical site of a patient, and defines an entrance point and an end point of a surgical instrument and a reference angle of the surgical instrument passing through the entrance point and the endpoint through the two-dimensional medical image and/or the three-dimensional medical image;
    a camera system, built in a pair of smart glasses, for capturing an image of the surgical site of the patient and a real-time dynamic image of a surgical instrument movement track;
    an image coincidence system for importing the three-dimensional medical image from the preoperative planning system and displaying the three-dimensional medical image on a display screen of the smart glasses, wherein the three-dimensional medical image would coincide with a real field of view of a doctor viewing the surgical site of the patient;
    a real-time surgical instrument tracking system, which, based on the real-time dynamic image of a surgical instrument movement track captured by the camera system, performs the following:
    (a) calculating in real-time a position difference between the tail point of the surgical instrument and the entrance point of the preoperative planning system; wherein the position difference is displayed through an entrance guiding interface, such that when the tail point of the surgical instrument is aligned with the entrance point, the entrance guiding interface displays an entrance aiming information, and when the tail point of the surgical instrument deviates from the entrance point, the entrance guiding interface displays an entrance deviation information;
    (b) calculating in real-time an angle difference between the tail point to a top point of the surgical instrument and the reference angle of the preoperative planning system; wherein the angle difference is displayed through an angle guiding interface, such that when the angle of the surgical instrument is aligned with the reference angle, the angle guiding interface displays an angle alignment information, and when the angle of the surgical instrument deviates from the reference angle, the angle guiding interface displays an angle deviation information; and
    (c) calculating in real-time a distance difference between the tail point of the surgical instrument and the end point of the preoperative planning system; wherein the distance difference is displayed through a depth guiding interface, such that when the tail point of the surgical instrument touches the end point, the depth guiding interface displays a touched information, and when there is a distance difference between the tail point of the surgical instrument and the end point, the depth guiding interface displays an untouched information;
    wherein the entrance guiding interface, the angle guiding interface, and the depth guiding interface are presented in the display screen of the smart glasses or in a real scene viewed through the smart glasses.

2. The surgical instrument guidance system according to claim 1, wherein when the entrance aiming information is displayed and maintained, the real-time surgical instrument tracking system performs an angle tracking of the surgical instrument; when both the entrance aiming information and the angle alignment information are displayed and maintained, the real-time surgical instrument tracking system performs a tracking between the tail point and end point of the surgical instrument; and when the entrance aiming information, the angle alignment information, and the touching information are all displayed and maintained indicating that the surgical instrument enters the patient's surgical site in accordance with the entrance point and the reference angle of preoperative planning system and touches the end point.

3. The surgical instrument guidance system according to claim 1, wherein the entrance guiding interface, the angle guiding interface, and the depth guiding interface are displayed on the display screen of the smart glasses together and not coincided with the three-dimensional medical images displayed on the display screen of the smart glasses firstly.

4. A method for real-time tracking of a surgical instrument, comprising the steps of:
    importing a two-dimensional medical image and a three-dimensional medical image of a surgical site of a patient through a preoperative planning system;
    through the two-dimensional medical image and/or the three-dimensional medical image, defining an entrance point and an end point of a surgical instrument and a reference angle of surgical instrument passing through the entrance point and the endpoint, and the entrance point, the end point and the reference angle are kept in the preoperative planning system;
    through a camera system built in a pair of smart glasses wore on a doctor, capturing an image of the surgical site of the patient and a real-time dynamic image of a surgical instrument movement track;

through an image coincidence system, displaying the three-dimensional medical image from the preoperative planning system on a display screen of the smart glasses, and adjusting an angle of the three-dimensional medical image on the display screen according to a focal length and a viewing angle of the doctor's eyes to cause the three-dimensional medical images to coincide with a real field of view of a doctor viewing the surgical site of the patient;

using the real-time dynamic image of the surgical instrument movement track through a real-time surgical instrument tracking system to (a) calculate in real-time a position difference between the tail point of the surgical instrument and the entrance point of the preoperative planning system; wherein the position difference is displayed through an entrance guiding interface in the display screen of the smart glasses or in a real scene viewed through the smart glasses, such that when the tail point of the surgical instrument is aligned with the entrance point, the entrance guiding interface displays an entrance aiming information, and when the tail point of the surgical instrument deviates from the entrance point, the entrance guiding interface displays an entrance deviation information;

(b) when the entrance aiming information is displayed and maintained, to calculate in real-time an angle difference between the tail point to a top point of the surgical instrument and the reference angle of the preoperative planning system, wherein the angle difference is displayed through an angle guiding interface in the display screen of the smart glasses or in the real scene viewed through the smart glasses, such that when the angle of the surgical instrument is aligned with the reference angle, the angle guiding interface displays an angle alignment information, and when the angle of the surgical instrument deviates from the reference angle, the angle guiding interface displays an angle deviation information; and (c) when both the entrance aiming information and the angle alignment information are displayed and maintained, to calculate in real-time a distance difference between the tail point of the surgical instrument and the end point of the preoperative planning system, wherein the distance difference is displayed through a depth guiding interface in the display screen of the smart glasses or in the real scene viewed through the smart glasses, such that when the tail point of the surgical instrument touches the end point, the depth guiding interface displays a touched information, and when there is a distance difference between the tail point of the surgical instrument and the end point, the depth guiding interface displays an untouched information; and when the entrance aiming information, the angle alignment information, and the touching information are all displayed and maintained, indicating that the surgical instrument enters the patient's surgical site in accordance with the entrance point and the reference angle of the preoperative planning system and touches the end point.

5. The method of claim 4, wherein the entrance guiding interface displays the entrance aiming information in a first color and the entrance deviation information in a second color; and the angle guiding interface displays the angle alignment information in the first color and the angle deviation information in the second color; the depth guiding interface displays the touched information in the first color and the untouched information in the second color.

6. The method of claim 4, wherein the entrance guiding interface, the angle guiding interface and the depth guiding interface respectively indicate the entrance point, the reference angle and the end point by a fixed mark; the entrance guiding interface, the angle guiding interface and the depth guiding interface respectively represent the position, the angle and the depth of the surgical instrument with a displacement mark moving in real-time according to the surgical instrument movement track, when the displacement mark is consistent with the fixed mark, the entrance aiming information, or the angle alignment information, or the touched information is displayed.

* * * * *